United States Patent [19]

Vogel

[11] Patent Number: 4,707,482
[45] Date of Patent: Nov. 17, 1987

[54] 4-(2,1,3-BENZOXADIAZOL AND BENZOTHIADIAZOL-4-4L)-1,4-DIHYDROPYRIDINE-3,5-DICARBOXYLIC ACID ESTERS USEFUL AS ANTIHYPERTENSIVES

[75] Inventor: Arnold Vogel, Riehen, Switzerland

[73] Assignee: Sandoz Ltd., Basel, Switzerland

[21] Appl. No.: 804,633

[22] Filed: Dec. 4, 1985

[30] Foreign Application Priority Data

Dec. 10, 1984 [DE] Fed. Rep. of Germany ....... 3444965

[51] Int. Cl.$^4$ .................. A61K 31/495; C07D 413/14; C07D 413/04; C07D 417/14
[52] U.S. Cl. .................................... 514/253; 514/333; 514/339; 544/364; 544/365; 544/368; 546/256; 546/271
[58] Field of Search ....................... 544/364, 365, 368; 514/253; 546/270, 271, 321

[56] References Cited

U.S. PATENT DOCUMENTS

| 4,031,104 | 6/1977 | Bossert et al. | 546/321 |
|---|---|---|---|
| 4,466,972 | 8/1984 | Neumann | 544/80 |
| 4,491,581 | 1/1985 | Vogel | 514/252 |
| 4,532,248 | 7/1985 | Franckowiak et al. | 514/302 |
| 4,537,881 | 8/1985 | Heiker et al. | 546/310 |
| 4,567,271 | 1/1986 | Neumann | 546/271 |
| 4,603,135 | 7/1986 | Meguro et al. | 514/252 |

FOREIGN PATENT DOCUMENTS

| 88276 | 9/1983 | European Pat. Off. |
| 94159 | 11/1983 | European Pat. Off. |
| 3239273 | 4/1984 | Fed. Rep. of Germany |
| 3400765 | 7/1985 | Fed. Rep. of Germany |

OTHER PUBLICATIONS

Meguro, Chem. Abst., 100-120900y, eq. EP 94159.
Wehinger et al., Chem. Abst. 100-22581a, eq. EP'88276.
Materne, Chem. Abst. 96-85553n, eq. EP 42089.
Meguro et al., Chem. Abst. eq. EP 94159.
Wehinger et al., Chem. Abst. 101-72619k, eq. EP'110073.
Neumann, Chem. Abst. 93-239419a.
Neumann, Chem. Abst. 93-239420u.
Neumann, Chem. Abst. 92-94404j, eq. US 4567271.
Dixon et al., Chem. Abst. 99-175596v.
Berthold, Chem. Abst. 96-205430u.
Vogel, Chem. Abst. 103-22595y, eq. EP'899937.
Vogel, CA 105-191098g.
Derwent Copy of Abstract JP 5717516 (10/82).

Primary Examiner—Donald G. Daus
Assistant Examiner—Cecilia Shen
Attorney, Agent, or Firm—Gerald D. Sharkin; Robert S. Honor; Joseph J. Borovian

[57] ABSTRACT 1,4-Dihydropyridine-3,5-dicarboxylic acid esters of formula I

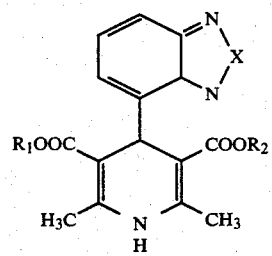

wherein the substitutents have various significances, are useful as calcium antagonists.

9 Claims, No Drawings

4-(2,1,3-BENZOXADIAZOL AND BENZOTHIADIAZOL-4-4L)-1,4-DIHYDROPYRIDINE-3,5-DICARBOXYLIC ACID ESTERS USEFUL AS ANTIHYPERTENSIVES

The present invention relates to 1,4-dihydropyridine derivatives, their preparation and pharmaceutical compositions containing them.

In particular the invention provides the compounds of formula I

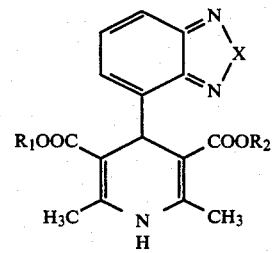

wherein X, $R_1$ and $R_2$ have the significance indicated below and the configuration at the carbon atom in the 4 position of the 1,4-dihydropyridinyl moiety is as indicated hereafter:

| Compound No. | X | $R_1$ | $R_2$ | Configuration |
|---|---|---|---|---|
| 1 | O | Me | $-(CH_2)_{10}N\diagup\diagdown N-CHPhe_2$ | (S) (+) |
| 2 | O | Me | $-(CH_2)_{10}OH$ | (S) (+) |
| 3 | O | Me | $-(CH_2)_{10}N\diagup\diagdown N-CHPhe_2$ | (R) (−) |
| 4 | O | Me | $-(CH_2)_{10}OH$ | (R) (−) |
| 5 | O | Me | $-(CH_2)_{10}N\diagup\diagdown N-CHPhe_2$ | (R,S) |
| 6 | O | Me | $-(CH_2)_{10}N\diagup\diagdown N-CH(p\text{-}F\text{-}Phe)_2$ | (S) (+) |
| 7 | O | Me | $-(CH_2)_{10}N\diagup\diagdown N-CH(p\text{-}F\text{-}Phe)_2$ | (R) (−) |
| 8 | O | Me | $-(CH_2)_{10}N\diagup\diagdown N-CH(p\text{-}F\text{-}Phe)_2$ | (R,S) |
| 9 | O | Me | $-(CH_2)_{10}N\diagup\diagdown-CHPhe_2$ | (S) (+) |
| 10 | O | Me | $-(CH_2)_{10}N\diagup\diagdown-CHPhe_2$ | (R) (−) |
| 11 | O | Me | $-(CH_2)_{10}N\diagup\diagdown-CHPhe_2$ | (R,S) |

-continued

| Compound No. | X | $R_1$ | $R_2$ | Configuration |
|---|---|---|---|---|
| 12 | O | Me | $-(CH_2)_{10}N\underset{\underset{\diagdown\diagup}{}}{\overset{\diagup\diagdown}{}}N-CH(p-MeO-Phe)_2$ | (S) (+) |
| 13 | O | Me | $-(CH_2)_{10}N\underset{\underset{\diagdown\diagup}{}}{\overset{\diagup\diagdown}{}}N-CH(p-MeO-Phe)_2$ | (R) (−) |
| 14 | O | Me | $-(CH_2)_{10}N\underset{\underset{\diagdown\diagup}{}}{\overset{\diagup\diagdown}{}}N-CH(p-MeO-Phe)_2$ | (R,S) |
| 15 | S | Me | $-(CH_2)_{10}N\underset{\underset{\diagdown\diagup}{}}{\overset{\diagup\diagdown}{}}N-CH(p-F-Phe)_2$ | (R,S) |
| 16 | S | Me | $-(CH_2)_{10}OH$ | (R,S) |
| 17 | O | iPr | $-(CH_2)_{10}N\underset{\underset{\diagdown\diagup}{}}{\overset{\diagup\diagdown}{}}CHPhe_2$ | (R) (+) |
| 18 | O | iPr | $-(CH_2)_{10}N\underset{\underset{\diagdown\diagup}{}}{\overset{\diagup\diagdown}{}}CHPhe_2$ | (S) (−) |
| 19 | O | iPr | $-(CH_2)_7N(Me)Bz$ | (R,S) |
| 20 | O | iPr | $-(CH_2)_7OH$ | (R,S) |
| 21 | O | iPr | $-(CH_2)_3N(Me)CH_2-\bigcirc\!\!\!\!\!\!\!\!\!\!\!\!\!\!\!\!\underset{OMe}{\overset{OMe}{}}$ | (R,S) |
| 22 | O | iPr | $-(CH_2)_3N(Me)CH_2CH_2-\bigcirc\!\!\!\!\!\!\!\!\!\!\!\!\!\!\!\!\underset{OMe}{\overset{OMe}{}}$ | (R,S) |
| 23 | O | iPr | $-(CH_2)_{10}N\underset{\underset{\diagdown\diagup}{}}{\overset{\diagup\diagdown}{}}NH$ | (R,S) |

Glossary:
Me = methyl  Phe = phenyl  iPr = isopropyl hereinafter referred to as "the compounds of the invention".

Some of the compounds of the invention fall under the very broad disclosures of Bayer EP 42 089, of Bayer EP 88 276, of Takeda EP 94 159 and/or of Bayer DOS 32 39 273.

None of the compounds specifically disclosed in the above-mentioned publications, however, falls under the scope of the present invention.

Further disclosures relating to compounds similar to the compounds of the invention are e.g.:
Sandoz EP 150
Sandoz DOS 29 49 464
Sandoz DOS 29 49 491
Sandoz BE 890 311
Bayer EP 71 819
Fisons EP 80 220
Sandoz DOS 33 20 616

The above-mentioned publications do not suggest any specific compounds similar to the compounds of the invention.

Further all the compounds of the present invention fall under the disclosure of Sandoz BE 899 937 and its equivalents, first published in Belgium on Dec. 18, 1984, i.e. at a date later than the priority date of the present invention, namely Dec. 10, 1984. None of the present compounds is specifically disclosed therein.

The compounds of the invention have a particularly interesting pharmacological profile.

One group of preferred compounds of the invention is compounds No. 1, 3, 5 to 15, 17 to 19 and 21 to 23, especially compounds No. 1, 3, 5 to 15, 17 and 18, in particular compounds No. 1, 3, 5 to 7 and 15, especially compounds No. 1, 3 and 5, in particular compound No. 1.

Another group of preferred compounds of the invention is compounds No. 1 to 7, 15, 16 and 19 to 23, preferably compounds 1, 3, 5 to 7, 15, 19 and 21 to 23.

Another group is compounds No. 2, 4, 16 and 20, particularly compound No. 2.

A further group is compounds No. 8 to 14, 17 and 18, particularly compounds No. 8, 12 to 14, 17 and 18.

In all the above subgroups are preferred those compounds which are in optically active form, especially those which are dextrorotatory, i.e., when $R_1$ is methyl, the (S) form and, when $R_1$ is isopropyl, the (R) form.

Especially preferred is compound No. 1.

A compound of the invention may be obtained by a process comprising appropriately converting a corresponding compound of formula II

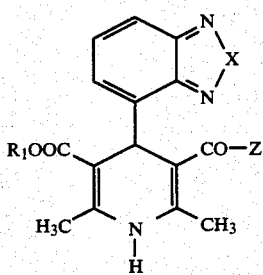

wherein $R_1$ and X are as defined above and

Z is a reactive group.

The process of the invention may be effected in a manner analogous to known processes.

The choice of the most appropriate process variant depends of course on the nature of the substituent $R_2$.

A process variant may e.g. be an esterification. A reactive group Z is then conveniently 1H-imidazol-1-yl. This process variant is indicated e.g. for converting into a hydroxyalkyl or substituted aminoalkyl substituent. A corresponding compound of formula II is thus reacted with a corresponding diol or aminoalcohol. As a solvent dioxane or an excess of the reaction partner may conveniently be used.

A further process variant may e.g. be an amination. This variant is indicated e.g. for converting into an aminoalkyl substituent. A reactive group Z is then conveniently a group —O—$(CH_2)_n$-Z' wherein n is 3, 7 or 10 and Z' is chlorine, bromine or a group $R_z$—$SO_2$—O— wherein $R_z$ is phenyl, tolyl or lower alkyl. Z' preferably is mesyloxy.

When potentially reactive groups such as secondary amino are present it may be indicated to effect the process of the invention with these groups in protected form, e.g. for a secondary amino in the form of a benzylamino group and to convert thereafter any protecting group present as such into the desired substituent, e.g. by hydrogenation.

A compound of the invention may be isolated from the reaction mixture and purified in a manner analogous to known methods.

A compound of the invention may exist in free form or where appropriate in acid addition salt form. A free form may be converted into an acid addition salt form in conventional manner and vice-versa. Suitable acids for acid addition salt formation include hydrochloric, malonic, p-toluene sulfonic and methanesulfonic acid.

Since the substituents in the 3 and 5 positions of the 1,4-dihydropyridinyl moiety are different the carbon atom in the 4 position is asymmetrically substituted. The compounds of the invention are in part racemates and in part individual enantiomers.

A compound used as a starting material may be obtained in conventional manner, e.g. by cyclization to a 1,4-dihydropyridinyl moiety.

Insofar as the preparation of any particular starting material is not particularly described, this may be effected in conventional manner or in analogous manner to that described herein.

In the following Examples all temperatures are in degrees Centigrade and are uncorrected.

EXAMPLE 1

(+)-(S)-4-(2,1,3-benzoxadiazo-4-yl)-1,4-dihydro-5-methoxycarbonyl-2,6-dimethyl-3-pyridine carboxylic acid-[10-[4-(diphenylmethyl)piperazin-1-yl]decyl]ester (amination) (compound No. 1)

64.2 g (+)-(S)-4-(2,1,3-benzoxadiazol-4-yl)-1,4-dihydro-5-methoxy-carbonyl-2,6-dimethyl-3-pyridine carboxylic acid-(10-methanesulfonyloxydecyl)ester and 57.5 g 1-diphenylmethylpiperazine are heated under refluxing for 22 hours in 2 l dioxan. The reaction mixture is then extracted with ice-water/ether-methylene chloride 4:1, the organic phase dried over magnesium sulfate and evaporated under reduced pressure. The product is chromatographed over silicagel using methylene chloride/ethanol 49:1 as an eluent. The product is dissolved in ether, the solution washed with ice-cold 1N aqueous sodium hydroxide, dried over magnesium sulfate and evaporated under reduced pressure. The resultant base is dried under high vacuum at 60°. The title compound is obtained (amorphous; $[\alpha]_D^{20} = +21°$; $[\alpha]_{546}^{20} = +30°$, ethanol, c=1 g/dl) (M.P. of the fumarate form 128°; $[\alpha]_D^{20} = +17°$; $[\alpha]_{546}^{20} = +25°$, ethanol, c=1 g/dl).

The (+)-(S)-mesylate used as a starting material is obtained from the compound of Example 2 as follows:

To a solution of 55.3 g of (+)-(S)-4-(2,1,3-benzoxadiazol-4-yl)-1,4-dihydro-5-methoxycarbonyl-2,6-dimethyl-3-pyridine carboxylic acid-(10-hydroxydecyl)ester and 59 ml of N-ethyl-diisopropylamine in 950 ml methylene chloride is added dropwise under stirring at 5° to 10° 13.3 ml of methanesulfonic acid chloride. After further agitation for 1 hour at 0° the mixture is extracted with cold 2N aqueous hydrochloric acid, the organic phase dried over magnesium sulfate and the solvent evaporated under reduced pressure (oil).

EXAMPLE 2

(+)-(S)-4-(2,1,3-benzoxadiazol-4-yl)-1,4-dihydro-5-methoxycarbonyl-2,6-dimethyl-3-pyridine carboxylic acid-(10-hydroxydecyl)ester (esterification) (compound No. 2)

242 g decan-1,10-diol are melted at 120° and 26.3 g (+)-(R)-4-(2,1,3-benzoxadiazol-4-yl)-1,4-dihydro-5-(1H)-imidazol-1-ylcarbonyl)-2,6-dimethyl-3-pyridine carboxylic acid methyl ester added. After 1 hour of stirring at 120° the mixture is allowed to cool, ether is added, the excess diol is filtered off, the solution is washed with ether and the organic phase evaporated under reduced pressure. The product is chromatographed over silicagel using methylene chloride/ethanol 19:1 as an eluent. The title compound is obtained (amorphous; $[\alpha]_D^{20} = +31°$; $[\alpha]_{546}^{20} = +44°$; ethanol, c=1 g/dl).

The (+)-(R)-imidazolide used as a starting material is obtained as follows:

(a) 2,1,3-Benzoxadiazol-4-carbaldehyde is reacted with aceto-acetic acid methyl ester in benzene in the presence of catalytic amounts of piperidine and acetic acid. The resultant 2-acetyl-3-(2,1,3-benzoxadiazol-4-yl)-2-propenoic acid methyl ester (crystalline, mixture of Z and E isomers) is cyclized in dioxane under refluxing with an equivalent amount of 3-aminocrotonic acid-(2-dimethylaminoethyl)ester {M.P. 56°; obtained by reaction of aceto-acetic acid-(2-dimethylaminoetyl)ester [B.P.$_{0.01\ mm}$ 140°-150°, obtained by reaction of diketen with 2-dimethylaminoethanol at 70°], with ammonia gas at 60°}, to give 4-(2,1,3-benzoxadiazol-4-yl)-1,4-dihydro-5-methoxycarbonyl-2,6-dimethyl-3-pyridine carboxylic acid-(2-dimethylaminoethyl)ester (M.P. 161°).

Alternatively this amine is also obtained by reaction of 4-(2,1,3-benzoxadiazol-4-yl)-1,4-dihydro-5-(1H-imidazol-1-ylcarbonyl)-2,6-dimethyl-3-pyridine carboxylic acid methyl ester (M.P. 224°) with 2-dimethylaminoethanol.

(b) 247 g of this amine are reacted with 249.4 g L-(−)-di-O,O'-p-toluoyltartaric acid hydrate in 2.5 l methanol at room temperature. The precipitated salt is recrystallized thrice from methanol, with the addition of methylene chloride for dissolution, and under heating. A tartrate is obtained (M.P. 180°; $[\alpha]_D^{20} = -25°$, $[\alpha]_{546}^{20} = -26°$, methanol, c=1 g/dl) containing 1 equivalent of (+)—(S)—base for 1 equivalent of L—(−)—acid.

This salt is converted into the free base by shaking it in a mixture of ether and cold 1N sodium hydroxide solution. (+)-(S)-4-(2,1,3-benzoxadiazol-4-yl)-1,4-dihydro-5-methoxycarbonyl-2,6-dimethyl-3-pyridine carboxylic acid-(2-dimethylaminoethyl)ester is obtained (M.P. 99° from ether/hexane; $[\alpha]_D^{20} = +55°$; $[\alpha]_{546}^{20} = +74°$, ethanol, c=1 g/dl).

(c) Quaternization of this (+)-(S)-amine with methyliodide gives the corresponding (+)-(S)-ammonium salt (M.P. 190°, $[\alpha]_D^{20} = +73°$, $[\alpha]_{546}^{20} = +99°$, methanol, c=1 g/dl).

(d) This (+)-(S)-ammonium salt is hydrolyzed in 2N sodium hydroxide solution and dioxane. (−)-(R)-4-(2,1,3-benzoxadiazol-4-yl)-1,4-dihydro-5-methoxycarbonyl-2,6-dimethyl-3-pyridine carboxylic acid is obtained (M.P. 175°; $[\alpha]_D^{20} = -4°$; $[\alpha]_{546}^{20} = -10°$, ethanol, c=1 g/dl).

(e) This (−)-(R)-carboxylic acid is reacted with 1,1'-carbonyl-diimidazole in dioxane at 50°. (+)-(R)-4-(2,1,3-benzoxadiazol-4-yl)-1,4-dihydro-5-(1H-imidazol-1-ylcarbonyl)-2,6-dimethyl-3-pyridine carboxylic acid methyl ester is obtained (M.P. 195°; $[\alpha]_D^{20} = +41°$; $[\alpha]_{546}^{20} = +60°$, ethanol, c=1 g/dl).

EXAMPLE 3

(−)-(R)-4-(2,1,3-benzoxadiazol-4-yl)-1,4-dihydro-5-methoxycarbonyl-2,6-dimethyl-3-pyridine carboxylic acid-[10-[4-(diphenylmethyl)piperazin-1-yl]-decyl]ester (compound No. 3)

The title compound is obtained starting from the corresponding (−)-(R)-mesylate in a manner analogous to Example 1 (amorphous; $[\alpha]_D^{20} = -20°$; $[\alpha]_{546}^{20} = -29°$, ethanol, c=1 g/dl).

The (−)-(R)-mesylate (oil) used as a starting material is obtained from the title compound of Example 4 in a manner analogous to that described in Example 1.

EXAMPLE 4

(−)-(R)-4-(2,1,3-benzoxadiazol-4-yl)-1,4-dihydro-5-methoxycarbonyl-2,6-dimethyl-3-pyridine carboxylic acid-(10-hydroxydecyl)ester (compound No. 4)

The title compound is obtained starting from the corresponding (−)-(S)-imidazolide is a manner analogous to Example 2 (amorphous; $[\alpha]_D^{20} = -31°$; $[\alpha]_{546}^{20} = -43°$, ethanol, c=1 g/dl).

The (−)-(S)-imidazolide used as a starting material is obtained in a manner analogous to that described in Example 2, step (a), and then for step (b) using D-(+)-di-O,O'-p-toluoyltartaric acid hydrate. The corresponding intermediates obtained are characterized as follows:

(b) Tartrate (M.P. 180°; $[\alpha]_D^{20} = +25°$; $[\alpha]_{546}^{20} = +26°$, methanol, c=1 g/dl) containing 1 equivalent of (−)-(R)-base for 1 equivalent of D-(+)-acid.

(−)-(R)-Base (M.P. 99° from ether/hexane; $[\alpha]_D^{20} = -55°$; $[\alpha]_{546}^{20} = -74°$, ethanol, c=1 g/dl).

(c) (−)-(R)-Ammonium salt (M.P. 190°; $[\alpha]_D^{20} = -73°$; $[\alpha]_{546}^{20} = -99°$, ethanol, c=1 g/dl).

(d) (+)-(S)-Carboxylic acid (M.P. 175°; $[\alpha]_D^{20} = +4°$; $[\alpha]_{546}^{20} = +10°$, ethanol, c=1 g/dl).

(e) (−)-(S)-Imidazolide (M.P. 195°; $[\alpha]_D^{20} = -41°$; $[\alpha]_{546}^{20} = -60°$, ethanol, c=1 g/dl).

EXAMPLE 5

4-(2,1,3-benzoxadiazol-4-yl)-1,4-dihydro-5-methoxycarbonyl-2,6-dimethyl-3-pyridine carboxylic acid[10-[4-(diphenylmethyl)piperazin-1-yl]decyl]ester (compound No. 5)

The title compound is obtained starting from the corresponding racemic mesylate in a manner analogous to Example 1 (free base and dihydrochloride forms: amorphous);

NMR-spectrum [(CDCl$_3$)$\delta$(ppm)]; 1.1-1.9 (16H, m), 2,32(s), 2,46(s), 2,23-2,8(16H), 3,6(3H, s), 3,98(2H, t, J=6Hz), 4,22(1H, s), 5,5(1H, s), 6,0(1H, s), 7,1-7,8(3H, m)

The racemic mesylate (oil) used as a starting material is obtained from the corresponding racemic decyl alcohol (oil) in a manner analogous to that described in Example 1. The racemic decyl alcohol is obtained in a manner analogous to Example 2, but leaving out fractionation step (b). The corresponding racemic intermediates obtained are characterized as follows:

(c) Ammonium salt (M.P. 180°)
(d) Carboxylic acid (M.P. 208°)
(e) Imidazolide (M.P. 224°)

The following compounds of formula I are obtained in analogous manner from the corresponding starting materials:

| Ex. No. and compound No. | Analogous to Ex. No. | X | R₁ | R₂ | Configuration at the 4 position of 1,4-dihydropyridinyl moiety | Physical characterization data | | |
|---|---|---|---|---|---|---|---|---|
| | | | | | | M.P. | $[\alpha]_D^{20}$ | $[\alpha]_{546}^{20}$ |
| 6 | 1⁽¹⁾;2 | O | Me | —(CH₂)₁₀N⟨piperidine⟩N—CH(p-F—Phe)₂ | (S) (+) | b amorphous | +19° | +28° (EtOH, c = 0.7 g/dl) |
| 7 | 1⁽²⁾;2 | O | Me | —(CH₂)₁₀N⟨piperidine⟩N—CH(p-F—Phe)₂ | (R) (−) | b amorphous | −20° | −28° (EtOH, c = 1.6 g/dl) |
| 8 | 1⁽³⁾;2 | O | Me | —(CH₂)₁₀N⟨piperidine⟩N—CH(p-F—Phe)₂ | (R,S) | b amorphous | NMR-spectrum⁽ᵍ⁾ | |
| 9 | 1⁽¹⁾;2 | O | Me | —(CH₂)₁₀N⟨piperidine⟩CHPhe₂ | (S) (+) | ch amorphous | +18° | +26° (EtOH, c = 0.7 g/dl) |
| 10 | 1⁽²⁾;2 | O | Me | —(CH₂)₁₀N⟨piperidine⟩CHPhe₂ | (R) (−) | ch amorphous | −20° | −27° (EtOH, c = 0.7 g/dl) |
| 11 | 1⁽³⁾;2 | O | Me | —(CH₂)₁₀N⟨piperidine⟩CHPhe₂ | (R,S) | b oil | | |
| 12 | 1⁽¹⁾;2 | O | Me | —(CH₂)₁₀N⟨piperidine⟩N—CH(p-MeO—Phe)₂ | (S) (+) | b amorphous | | |
| 13 | 1⁽²⁾;2 | O | me | —(CH₂)₁₀N⟨piperidine⟩N—CH(p-MeO—Phe)₂ | (R) (−) | b amorphous | | |

-continued

The following compounds of formula I are obtained in analogous manner from the corresponding starting materials:

| Analogous to Ex. No. | X | R₁ | R₂ | Configuration at the 4 position of 1,4-dihydropyridinyl moiety | Physical characterization data | | |
|---|---|---|---|---|---|---|---|
| | | | | | M.P. | $[\alpha]_D^{20}$ | $[\alpha]_{546}^{20}$ |
| 14 | O | Me | −(CH₂)₁₀N⟨piperidine⟩N−CH(p-MeO−Phe)₂ | b amorphous | NMR-spectrum(h) | | |
| 15 | S | Me | −(CH₂)₁₀N⟨piperidine⟩N−CH(p-F−Phe)₂ | (R,S) | b amorphous | NMR-spectrum(a) | |
| 16 | S | Me | −CH₂)₁₀OH | (R,S) | n oil | | |
| 17 | O | iPr | −(CH₂)₁₀N⟨piperidine⟩−CHPhe₂ | (R) (+) | ch amorphous | +13° | +17° (EtOH, c = 0.6 g/dl) |
| 18 | O | iPr | −(CH₂)₁₀N⟨piperidine⟩−CHPhe₂ | (S)M (−) | ch amorphous | −13° | −17° (EtOH, c = 0.6 g/dl) |
| 19 | O | iPr | −(CH₂)₇N(Me)Bz | (R,S) | ch amorphous | NMR-spectrum(e) | |
| 20 | O | iPr | −(CH₂)₇OH | (R,S) | n amorphous | NMR-spectrum(f) | |
| 21 | O | iPr | −(CH₂)₃N(Me)CH₂−⟨Ph(OMe)₂⟩ | (R,S) | ch amorphous | NMR-spectrum(c) | |
| 22 | O | iPr | −(CH₂)₃N(Me)CH₂CH₂−⟨Ph(OMe)₂⟩ | (R,S) | ch amorphous | NMR-spectrum(d) | |
| 23 | O | iPr | −(CH₂)₁₀N⟨piperazine-NH⟩ | (R,S) | b amorphous | NMR-spectrum(b) | |

-continued

The following compounds of formula I are obtained in analogous manner from the corresponding starting materials:

| Example No. | Compound No. | Analogous to Ex. No. | X | R₁ | R₂ | Configuration at the 4 position of 1,4-dihydropyridinyl moiety | Physical characterization data M.P. | $[\alpha]_D^{20}$ | $[\alpha]_{546}^{20}$ |
|---|---|---|---|---|---|---|---|---|---|
| 24 | 1 | 2(12) | O | Me | —CH₂)₁₀N⌬N—CHPhe₂ | (S) (+) | see Example 1 | | |
| 25 | 3 | 2(12) | O | Me | —CH₂)₁₀N⌬N—CHPhe₂ | (R) (−) | see Example 3 | | |
| 26 | 5 | 2(12) | O | Me | —CH₂)₁₀N⌬N—CHPhe₂ | (R,S) | see Example 5 | | | b = in free base form
Me = methyl
iPr = isopropyl
ch = in hydrochloric acid addition salt form
Et = ethyl
n = in free neutral form
Phe = phenyl NMR-spectra (CDCl₃ if not otherwise specified) (ppm):
(a)1,2(16H,m) 2,2–2,6(16H), 2.33(s), 2.36(s), 2.45(s), 1.52(3H,s), 3,9(2H,s), 4.22(1H,s), 5,74(1H,s), 5,84(1H,s), 6,85–7,9(11H,m).
(b)(DMSO): 0,75–1,4(22H,m), 2,3(6H,s), 3,0–3,9(12H,m), 4,8(1H,m), 5,42(1H,s) 7,2–7,9(3H,m), 9,15(1H,s), 9,9(2H,wide), 11,9(1H,wide).
(c)0,9(3H,d), 1,22(3H,d), 1,8–3,1(13H), 2,34(s), 2,37(s), 3,87–4,2(10H), 3,9(s), 3,98(s), 4,9(1H,m), 5,52(1H,s), 6,5–7,7(7H,m).
(d)0,82(3H,d), 1,15(3H,d), 2,18(2H,m), 2,38(3H,wide), 3,2(6H,wide), 3,88(3H,s), 3,9(3H,s), 4,1(2H,m), 4,9(1H,m), 5,52(1H,s), 6,75–7,75(6H,m), 11,7(2H,wide).
(e)0,92(3H,d), 1,0–2,0(13H,m), 2,35(6H,wide), 2,72(3H,s), 2,9(2H,m), 3,95(2H,t), 4,2(2H,s), 4,9(1H,m), 5,5(1H,s), 6,8(1H,s), 7,2–7,75(8H,m).
(f)0,98(3H,d), 1,24(3H,d), 1,2–1,9(11H,m), 2,34(6H,s), 3,6(6H,t), 4,01(2H,t), 4,94(1H,m), 5,52(1H,s), 6,45(1H,s), 6,83–7,7(11H,m).
(g)1,1–1,7(16H,m), 2,3–2,5(16H), 3,6(3H,s), 3,97(2H,t), 4,21(1H,s), 5,46(1H,s), 5,92(1H,s), 6,75–7,7(11H,m).
(h)1,1–1,6(16H,m), 2,2–2,55(16H), 3,6(3H,s), 3,76(6H,s), 3,97(2H,t), 4,14(1H,s), 5,46(1H,s), 6,0(1H,s), 6,75–7,7(11H,m).
(1)Starting from the compound of Example 4.
(2)Starting from the compound of Example 2.
(3)Starting from the corresponding racemic decyl alcohol described in Example 5.
(4)Starting from the corresponding mesylate prepared from the compound of Example 16 in a manner analogous to that described in Example 1.
(5)Starting from 4-(2,1,3-benzothiadiazol)-4-yl)-1,4-dihydro-5-(1H—imidazol-1-ylcarbonyl)2,6-dimethyl-3-pyridine carboxylic acid methyl ester by reaction with decan-1,10-diol and chromatography over silicagel using methylene chloride/ethanol 19:1 as an eluent.
(6)Starting from (+)-(R)-4-(2,1,3-benzoxadiazol-4-yl)-1,4-dihydro-5-isopropoxycarbonyl-2,6-dimethyl-3-pyridine carboxylic acid-(10-methansulfonyloxydecyl)ester obtained as an oil starting from (+)-(R)-4-(2,1,3-benzoxadiazol-4-yl)-1,4-dihydro-5-isopropoxycarbonyl-2,6-dimethyl-3-pyridine carboxylic acid-(10-hydroxydecyl)ester (oil; $[\alpha]_D^{20} = +20$; $[\alpha]_{546}^{20} = +28°$, EtOH, c = 1 g/dl). This alcohol is obtained in a manner analogous to Example 2 from the corresponding imidazolide. The imidazolide enantiomer is obtained in a manner analogous to Example 2, steps (a) to (e).
(7)Using the enantiomers of the compounds described under footnote(6).
(8)Starting from the compound of Example 20 via the corresponding mesylate.
(9)Starting from 4-(2,1,3-benzoxadiazol-4-yl)-1,4-dihydro-5-(1H—imidazol-1-ylcarbonyl)-2,6-dimethyl-3-pyridine carboxylic acid isopropyl ester.
(10)Starting from 4-(2,1,3-benzoxadiazol-4-yl)-1,4-dihydro-5-isopropoxycarbonyl-2,6-dimethyl-3-pyridine carboxylic acid-(3-methansulfonyloxypropyl)ester obatined as an oil starting from 4-(2,1,3-benzoxadiazol-4-yl)-1,4-dihydro-5-isopropoxycarbonyl-2,6-dimethyl-3-pyridine carboxylic acid-(3-hydroxypropyl)ester (oil). This alcohol is obtained from the imidazolide described in footnote(9).
(11)4-(2,1,3-benzoxadiazol-4-yl)-1,4-dihydro-5-isopropoxycarbonyl-2,6-dimethyl-3-pyridine carboxyl acid-[10-(4-benzylpiperazin-1-yl)decyl]ester (oil) is first prepared from the corresponding mesylate in a manner analogous to Example 1 and then the dihydrochloride thereof (amorphous) is debenzylated by hydrogenation in methanol over 10% palladium on charcoal at room temperature. The mesylate is obtained as an oil from 4-(2,1,3-benzoxadiazol-4-yl)-1,4-dihydro-5-isopropoxycarbonyl-2,6-dimethyl-3-pyridine carboxyl acid-(10-hydroxydecyl)ester. This alcohol is obtained as an oil from 4-(2,1,3-benzoxadiazol-4-yl)-1,4-dihydro-5-(1H—imidazol-1-yl)-2,6-dimethyl-3-pyridine carboxyl acid isopropyl ester in a manner analogous to Example 2.
(12)By esterification of the corresponding imidazolide with 10-[4-(diphenylmethyl)piperazin-1-yl)]decan-1-ol.

The compounds of the invention are useful because they possess pharmacological activity.

The compounds exhibit effects typical of calcium antagonists. They exhibit a pronounced muscle-relaxing effect, particularly on smooth muscle, as evidenced by vasodilating and blood pressure lowering activity in standard tests. For example in the anaesthetized cat test using tracer microspheres (R. Hof et al., *Basic Res. Cardiol.* 75 [1980] 747–756 and 76 [1981] 630–638; (R. Hof et al., *J. Cardiovasc. Pharmacol.* 4 [1982] 352–362) coronary vasodilation, an increase in skeletal muscle blood flow and a fall in blood pressure are observed upon intravenous administration of from about 3 to about 300 μg/kg, e.g. of from about 10 to about 100 μg/kg.

A fall in blood pressure is also observed in the conscious spontaneously hypertensive rat (method of Gerold and Tschirki, *Arzneimittelforschung* 18 [1968] 1285) upon administration of from about 0.03 mg/kg to about 10 mg/kg p.o. of the compounds.

In the anaesthetized rat test a fall in blood pressure is also observed upon intravenous administration of from about 3 to about 300 μg/kg, e.g. for the compound of Example 1 of from about 30 to about 100 μg/kg.

The test method is as follows:

Male Wistar rats are anaesthetized with 140 mg/kg thiobarbital, The trachea cannulated and the animals allowed to breathe normal room air. The femoral artery is cannulated for the recording of blood pressure and heart rate via a Statham pressure transducer and the drug is infused into the femoral artery over a 15-minute period in a total volume of 1 ml. Body temperature is maintained at 36° C. After an initial stabilization period of about 1 hour blood pressure and heart rate remain stable under these conditions for more than 6 hours, allowing the effects of drugs on these parameters to be monitored.

The compounds are longer acting than known standard compounds, they are suitable e.g. for once-a-day administration. The activity of the compound of Example 1 thus persists for at least 6 hours. The compounds are also particularly well-absorbed orally. They are particularly well-tolerated.

The compounds are therefore useful as calcium antagonists for the prevention and treatment of
coronary insufficiency, e.g. Angina pectoris;
other disturbances in calculation e.g. in limbs such as
  intermittent claudication and spasms, e.g. cholic;
asthma, e.g. exertion-related asthma;
hypertension.

Preferred in this indication are compounds No. 1, 3, 5 to 14, 17 to 19 and 21 to 23, especially compounds No. 1 and 5, particularly compound No. 1.

The compounds also have a vasodilating activity on capillary vessels of the carotid area; the vasoconstrictor effect of serotonin is thereby antagonized and the associated dysregulation inhibited. This makes the compounds useful for the prevention and treatment of migraine and vascular headache such as cluster headache, especially for the interval treatment (prevention) of migraine. They are more potent and effective than flunarizine. Preferred in this indication are the compounds having a relatively moderate effect on blood pressure and peripheral blood vessels.

Preferred in this indication are compounds No. 15 and 16, particularly compound No. 15.

Preferred is the use against hypertension.

For the above-mentioned uses the dosage will, of course, vary depending on the compound employed, mode of administration and treatment desired. However, in general, satisfactory results are obtained when administered at a daily dosage of from about 5 μg to about 3 mg per kg animal body weight, conveniently given in divided doses 1 to 3 times a day or in sustained release form. For the larger mammal the total daily dosage is in the range of from about 0.3 mg to about 200 mg, and dosage forms suitable for oral or non-oral administration comprise from about 0.1 mg to about 100 mg of the compounds admixed with a solid or liquid pharmaceutical carrier or diluent. An example of a daily dosage is from about 0.3 mg to about 10 mg.

The compounds may thus be administered in similar manner to known standards, for example verapamil or diltiazem. They do, however, not possess the disadvantages exhibited by those two compounds, e.g. cardiodepression for verapamil and bradyarrhythmias for diltiazem. The suitable daily dosage for a particular compound will depend on a number of factors such as its relative potency of activity. It has for example been determined that one of the preferred compounds of this invention, i.e. the title compound of Example 1, is active in the above-mentioned anaesthetized cat test using tracer microspheres at a dose of from about 30 to about 100 μg/kg i.v. as compared to a dose of from about 300 to about 1000 μg/kg i.v. for verapamil and diltiazem. It is therefore indicated that the compounds may be administered at similar or lower dosages than conventionally employed for verapamil and diltiazem.

The compounds of the invention may be administered in free form or where appropriate in pharmaceutically acceptable acid addition salt form. Such salt forms exhibit the same order of activity as the free forms and are readily prepared in conventional manner. The present invention also provides a pharmaceutical composition comprising a compound of the invention in free form or where appropriate in pharmaceutically acceptable salt form, in association with a pharmaceutical carrier or diluent. Such compositions may be in the form of, for example, a capsule suitable e.g. for sublingual administration, or a tablet.

I claim:

1. A compound of formula I:

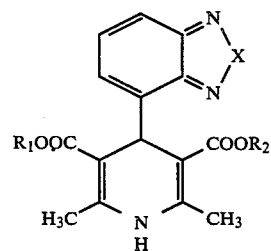

wherein X, $R_1$ and $R_2$ have the significances indicated below and the configuration at the carbon atom in the 4 position of the 1,4-dihydropyridinyl moiety is as indicated hereafter:

| Compound No. | X | $R_1$ | $R_2$ |
|---|---|---|---|

-continued

| | | | |
|---|---|---|---|
| 1 | O | Me | —(CH₂)₁₀N⟨piperazine⟩N—CHPhe₂ |
| 2 | O | Me | —(CH₂)₁₀N⟨piperazine⟩N—CHPhe₂ |
| 3 | O | Me | —(CH₂)₁₀N⟨piperazine⟩N—CHPhe₂ |
| 4 | O | Me | —(CH₂)₁₀N⟨piperazine⟩N—CH(p-F—Phe)₂ |
| 5 | O | Me | —(CH₂)₁₀N⟨piperazine⟩N—CH(p-F—Phe)₂ |
| 6 | O | Me | —(CH₂)₁₀N⟨piperazine⟩N—CH(p-F—Phe)₂ |
| 7 | O | Me | —(CH₂)₁₀N⟨piperazine⟩N—CH(p-MeO—Phe)₂ |
| 8 | O | Me | —(CH₂)₁₀N⟨piperazine⟩N—CH(p-MeO—Phe)₂ |
| 9 | O | Me | —(CH₂)₁₀N⟨piperazine⟩N—CH(p-MeO—Phe)₂ |
| 10 | S | Me | —(CH₂)₁₀N⟨piperazine⟩N—CH(p-F—Phe)₂ |
| 11 | O | iPr | —(CH₂)₁₀N⟨piperazine⟩NH |

Compound

| No. | Configuration | |
|---|---|---|
| 1 | (S) | (+) |
| 2 | (R) | (−) |
| 3 | (R,S) | |
| 4 | (S) | (+) |
| 5 | (R) | (−) |
| 6 | (R,S) | |
| 7 | (S) | (+) |
| 8 | (R) | (−) |
| 9 | (R,S) | |
| 10 | (R,S) | |
| 11 | (R,S) | | in free base or, where appropriate, in pharmaceutically acceptable acid addition salt form.

2. The compound of claim 1 which is (+)-(S)-4-(2,1,3-benzoxadiazol-4-yl)-1,4-dihydro-5-methoxycarbonyl-2,6-dimethyl-3-pyridine carboxylic acid-[10-[4-(diphenylmethyl)piperazin-1-yl]decyl]ester in free form or in pharmaceutically acceptable acid addition salt form.

3. The compound of claim 1 which is 4-(2,1,3-benzoxadiazol-4-yl)-1,4-dihydro-5-methoxycarbonyl-2,6-dimethyl-3pyridine carboxylic acid-[10-[4-(diphenylmethyl)piperazin-1-yl]decyl]ester in free form or in pharmaceutically acceptable acid addition salt form.

4. A pharmaceutical composition useful in treating coronary insufficiency, disturbances in circulation, asthma, hypertension or migraine and vascular headaches comprising a pharmaceutically acceptable carrier or diluent and a therapeutically effective amount of a compound of claim 1, in free form or in pharmaceutically acceptable acid addition salt form.

5. A method of treating coronary insufficiency comprising administering to a subject in need of such treatment a therapeutically effective amount of a compound of claim 1, in free form or in pharmaceutically acceptable acid addition salt form.

6. A method of treating disturbances in circulation comprising administering to a subject in need of such treatment a therapeutically effective amount of a compound of claim 1, in free form or in pharmaceutically acceptable acid addition salt form.

7. A method of treating asthma comprising administering to a subject in need of such treatment a therapeutically effective amount of a compound of claim 1, in free form or in pharmaceutically acceptable acid addition salt form.

8. A method of treating hypertension comprising administering to a subject in need of such treatment a therapeutically effective amount of a compound of claim 1, in free form or in pharmaceutically acceptable acid addition salt form.

9. A method of treating migraine and vascular headaches comprising administering to a subject in need of such treatment a therapeutically effective amount of a compound of claim 1, in free form or in pharmaceutically acceptable acid addition salt form.

* * * * *